United States Patent
Zyck et al.

(10) Patent No.: US 7,244,454 B1
(45) Date of Patent: Jul. 17, 2007

(54) CHEWING GUM PRODUCT INCLUDING ENCAPSULATED ASPARTAME AND SODIUM BICARBONATE AND PROCESS OF PREPARING

(75) Inventors: Daniel J. Zyck, North Riverside, IL (US); Robert Yatka, Orland Park, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 0 days.

(21) Appl. No.: 09/554,295

(22) PCT Filed: Dec. 3, 1997

(86) PCT No.: PCT/US97/22437

§ 371 (c)(1),
(2), (4) Date: Aug. 7, 2000

(87) PCT Pub. No.: WO99/27798

PCT Pub. Date: Jun. 10, 1999

(51) Int. Cl.
*A23G 3/30* (2006.01)

(52) U.S. Cl. .......................................................... 426/3

(58) Field of Classification Search .................... 426/3, 426/5; 424/48, 440
See application file for complete search history.

(56) References Cited

U.S. PATENT DOCUMENTS

| | | |
|---|---|---|
| 3,590,120 A | 6/1971 | Muhler |
| 4,269,860 A | 5/1981 | Ogawa et al. |
| 4,384,004 A | 5/1983 | Cea et al. |
| 4,639,368 A | 1/1987 | Niazi et al. |
| 4,673,577 A | 6/1987 | Patel |
| 4,824,681 A | 4/1989 | Schobel et al. |
| 4,863,745 A | 9/1989 | Zibell |
| 4,911,934 A | 3/1990 | Yang et al. |
| 4,931,295 A | 6/1990 | Courtright et al. |
| 4,981,698 A | 1/1991 | Cherukuri et al. |
| 4,997,659 A | 3/1991 | Yatka et al. |
| 5,112,625 A | 5/1992 | Zibell et al. |
| 5,154,939 A | 10/1992 | Broderick et al. |
| 5,164,210 A | 11/1992 | Campbell et al. |
| 5,165,944 A | 11/1992 | Song et al. |
| 5,192,561 A | 3/1993 | Bunczek et al. |
| 5,217,735 A | 6/1993 | Zibell |
| 5,221,543 A | 6/1993 | Zibell et al. |
| 5,364,627 A | 11/1994 | Song |
| 5,433,960 A | 7/1995 | Meyers |
| 5,618,517 A | 4/1997 | Miskewitz |
| 5,629,035 A | 5/1997 | Miskewitz |
| 5,693,334 A | 12/1997 | Miskewitz |

FOREIGN PATENT DOCUMENTS

| | | |
|---|---|---|
| JP | 60-270819 | 6/1987 |
| JP | 1992-158746 | 6/1992 |
| WO | 96/20608 | 7/1996 |
| WO | 97/12589 | 4/1997 |

*Primary Examiner*—Arthur L. Corbin
(74) *Attorney, Agent, or Firm*—Bell, Boyd & Lloyd LLC

(57) ABSTRACT

Chewing gum formulations including sodium bicabornate and encapsulated aspartame are disclosed. Methods of manufacturing chewing gum are also disclosed.

19 Claims, 4 Drawing Sheets

Aspartame Loss With 0% Sodium Bicarbonate

Aspartame Loss With 1% Sodium Bicarbonate

CHEWING GUM PRODUCT INCLUDING ENCAPSULATED ASPARTAME AND SODIUM BICARBONATE AND PROCESS OF PREPARING

BACKGROUND OF THE INVENTION

The present invention generally relates to chewing gum. More specifically, the present invention relates to chewing gums including aspartame.

It is of course known to prepare chewing gum including a variety of different ingredients. Some of these ingredients are used to add a flavor or sweetness to the chewing gum. One of the difficulties encountered in adding certain ingredients to chewing gum is that they are vulnerable to degradation.

One of the ingredients that has been recently added to chewing gum formulations are high intensity sweeteners. One such high intensity sweetener is aspartame. Aspartame is a sweetener that has been approved for use in food products including chewing gum in the United States and many different countries. One of the difficulties in using aspartame in chewing gum is that it is vulnerable to degradation; upon exposure to moisture, aspartame will degrade.

Another ingredient that has been used in chewing gum products is sodium bicarbonate or baking soda. Sodium bicarbonate provides chewing gum with dental health benefits. These benefits include possible tooth whitening.

Generally, sodium bicarbonate containing chewing gums are sugarless. Thus, these gums may desirably include aspartame. However, when chewing gum including sodium bicarbonate is provided due to its higher pH, the aspartame becomes less stable in the product. Indeed, the greater amount of sodium bicarbonate used in the formula, the lower the stability of the aspartame in the formula. This results in a chewing gum product wherein the aspartame degrades. Thus, although desirable, such chewing gum products including sodium bicarbonate and aspartame are very problematic.

SUMMARY OF THE INVENTION

The present invention provides improved chewing gums including aspartame and methods of manufacturing same. Pursuant to the present invention, chewing gum compositions including sodium bicarbonate, are provided that also include encapsulated aspartame. It has been found that by using encapsulated aspartame in gum formulas that contain sodium bicarbonate that the loss of aspartame during the shelf life of the chewing gum product is virtually eliminated.

To this end, the present invention provides a chewing gum comprising a water insoluble gum base portion and a water soluble portion including sodium bicarbonate and encapsulated aspartame.

In an embodiment, sodium bicarbonate comprises approximately 0.1% to about 1% by weight of the chewing gum.

In an embodiment, aspartame comprises approximately 0.01% to about 1% by weight of the chewing gum.

In an embodiment, the aspartame is coated with at least one food grade material selected from the group consisting of shellac, Zein, agar, alginate, cellulose derivatives, dextrin, gelatin, modified starch, acacia and maltodextrin.

In an embodiment, the encapsulated aspartame comprises at least 20% coating.

In an embodiment, the moisture level of the chewing gum is not greater than 2%.

In an embodiment, the aspartame is encapsulated by agglomeration.

In an embodiment, the aspartame is encapsulated by coating a food grade material onto the aspartame.

In a further embodiment, a chewing gum is provided that comprises a water insoluble base portion and a water soluble portion including at least 0.1% by weight sodium bicarbonate and at least 0.01% by weight encapsulated aspartame.

In another embodiment of the present invention, a method for producing chewing gum including aspartame and sodium bicarbonate is provided comprising the steps of adding to a water insoluble base portion, encapsulated aspartame and sodium bicarbonate.

In an embodiment, the encapsulated aspartame and sodium bicarbonate is added to the water insoluble base portion with a flavor.

In an embodiment, the step of encapsulating the aspartame is by coating a food grade material onto the aspartame.

In an embodiment, the step of encapsulating the aspartame is by agglomerating an agent onto the aspartame.

In an embodiment, the step of encapsulating the aspartame is by using a two-step process.

In an embodiment, the step of encapsulating the aspartame is by using a process wherein aspartame is absorbed onto another component.

It is an advantage of the present invention to provide an improved chewing gum formulation.

Another advantage of the present invention is to provide an improved chewing gum formulation including sodium bicarbonate.

Still further, an advantage to the present invention is to provide an improved chewing gum formulation that is sugarless, and includes sodium bicarbonate as well as aspartame.

Furthermore, an advantage of the present invention is that it provides improved methods for preparing chewing gum formulations including aspartame.

Moreover, an advantage to the present invention i5 that it provides chewing gum formulations including aspartame as well as sodium bicarbonate, wherein the loss of aspartame during the shelf life of the chewing gum product is effectively eliminated.

Additional features and advantages of the present invention are described in, and will be apparent from, the Detailed Description of the Presently Preferred Embodiments and from the Figures.

DETAILED DESCRIPTION OF THE PRESENTLY PREFERRED EMBODIMENTS

The present invention provides improved chewing gum formulations and methods of manufacturing same. Pursuant to the present invention, encapsulated aspartame is provided in chewing gum formulations including sodium bicarbonate. It has been surprisingly found that the use of encapsulated aspartame with sodium bicarbonate virtually eliminates the loss of aspartame.

As noted above, although it is desirable to use sodium bicarbonate in at least certain chewing gum formulations to provide dental health benefits such as tooth whitening, there are drawbacks to the use of such product. In this regard, it is desirable for such products to be sugarless. However, it has been found that when aspartame is used with sodium bicarbonate, the aspartame becomes less stable and subject to degradation. Indeed, the greater the amount of sodium bicarbonate used in a gum formulation the lower the stability of the aspartame in the formula.

It has been surprisingly found that the use of encapsulated aspartame in a chewing gum formula that contains sodium bicarbonate virtually eliminates the loss of aspartame during the shelf life of the product. As set forth in detail below, the type of encapsulation does not appear to affect the results achieved by the present invention. Therefore, the aspartame can be encapsulated using methods such as coating, encapsulation, agglomeration, absorption, or extrusion. As is also noted below, preferably the chewing gum will have a reduced moisture preferably less then 2%. Most preferably the chewing gum will have a reduced moisture of 1% or less.

By way of example and not limitation, the examples below demonstrate the effect sodium bicarbonate has on the stability of aspartame in chewing gum.

EXAMPLES A THROUGH E

The following gum formulas were made:

|  | A | B | C | D | E |
|---|---|---|---|---|---|
| Base | 25.20 | 25.20 | 25.20 | 25.20 | 25.20 |
| Sorbitol | 51.79 | 51.54 | 51.29 | 50.79 | 49.75 |
| Mannitol | 4.25 | 4.25 | 4.25 | 4.25 | 4.25 |
| Coevaporated Lycasin/Glycerin | 8.50 | 8.50 | 8.50 | 8.50 | 8.50 |
| Glycerin | 8.50 | 8.50 | 8.50 | 8.50 | 8.50 |
| Flavor | 1.20 | 1.20 | 1.20 | 1.20 | 1.20 |
| Sodium Bicarbonate | 0.00 | 0.25 | 0.50 | 1.00 | 2.00 |
| Lecithin | 0.16 | 0.16 | 0.16 | 0.16 | 0.16 |
| Free Aspartame | 0.40 | 0.40 | 0.40 | 0.40 | 0.40 |
| pH | 6.65 | 6.73 | 6.84 | 7.23 | 7.36 |

Figure 1:
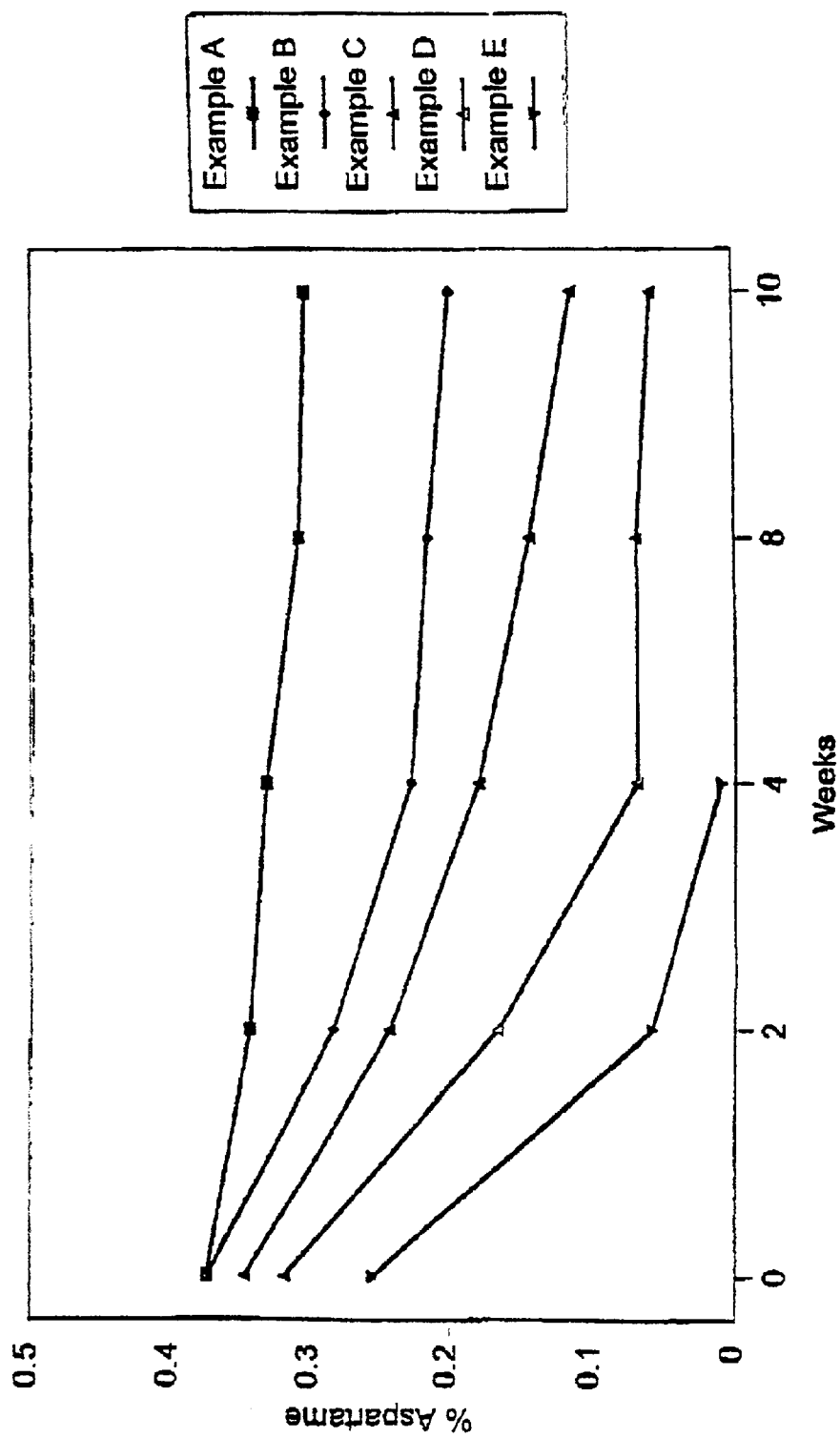
FIG. 1 illustrates graphically aspartame loss in chewing gum with sodium bicarbonate; specifically percent of aspartame loss over time in weeks.

These chewing gum formulations were tested to determine the stability of aspartame in each of the formulations over time. The results of the analysis are set forth in FIG. 1; graphically aspartame loss over time (weeks) is illustrated in FIG. 1. As illustrated, the greater the level of sodium bicarbonate the lower the stability of aspartame.

To improve the stability of aspartame in gum formulas including sodium bicarbonate, pursuant to the present invention, aspartame is encapsulated. The aspartame may be encapsulated, agglomerated, absorbed, entrapped, or extruded with an encapsulating agent to protect it from degradation. For aspartame encapsulation, any standard technique which gives partial or full encapsulation, can be used. These techniques include, but are not limited to, spray drying, spray chilling, fluid-bed coating, and coacervation. These encapsulation techniques can be used individually or in any combination in a single step process or multiple step process.

The encapsulation techniques that can be used can give varying degrees of coating from partial to full coating depending on the coating composition used in the process. Also the coating compositions may be susceptible to water permeating to various degrees. Generally, compositions that have high organic solubility, good film forming properties, and low water solubility, provide a better encapsulation of aspartame. Such compositions include acrylic polymers and copolymers, carboxyvinyl polymers, polyamides, polystyrene, polyvinyl acetate, polyvinyl acetate phthalate, polyvinyl pyrrolidone, and waxes.

Although all of the above materials are possible for encapsulation of aspartame, only food grade materials should be used. Two standard food grade coating materials that are good formers, but not water soluble, are shellac and Zein. Others which are more water soluble, but also good film formers, are materials such as agar, alginates, a wide range of cellulose derivative like ethyl cellulose and hydroxypropylmethyl cellulose, dextrin, gelatin and modified starches. Other encapsulants like acacia or maltodextrin can also be used to encapsulate the aspartame.

Generally, the higher the level of coating and the lower the amount of aspartame, the higher the stability of aspartame. To obtain the desired encapsulation, the encapsulant should be at a minimum of about 20% of the coated product. Preferably, the encapsulant should be at a minimum of about 30% of the coated product, and most preferably should be at a minimum of about 40% of the coated product. Depending on the coating material, a higher or lower amount of coating material may be needed to provide the desired encapsulation.

Another method of partial encapsulation is agglomeration with an agglomerating agent which partially coats aspartame. This method includes the step of mixing the aspartame and agglomerating agent with a small amount of water or solvent. The mixture is prepared in such a way as to have individual wet particles in contact with each other so a partial coating can be applied. After the water or solvent is removed, the mixture is ground and used as a powdered coated encapsulated aspartame.

Materials that can be used as the agglomerating agent are the same as those used in the encapsulation previously mentioned. However, since the coating is only a partial encapsulation, some agglomeration agents are more effective than others. Some of the better agglomerating agents are organic polymers such as acrylic polymer and copolymers, polyvinyl acetate, polyvinyl-pyrrolidone, waxes, shellac and Zein. Other agglomerating agents may not be as effective as are the polymers, waxes, shellac and Zein. These other agglomerating agents include, but are not limited to, agar, alginates, a wide range of cellulose derivatives, dextrin, gelatin, modified starches, and vegetable gums such as guar gums, locust bean gum, and carrageenan.

Even though the agglomerated aspartame is only partially coated, when the quantity of coating is increased compared to the quantity of aspartame, improved aspartame stability is obtained. The level of coating used in the agglomerated product should be at a minimum about 5%. Preferably the coating level is at a minimum about 15%, and more preferably about 20%.

Aspartame may be coated in a two-step process or multiple step process. Aspartame may be encapsulated with any of the materials previously described and then the encapsulated material can be agglomerated as previously described to obtain an encapsulated/agglomerated product that could be used in chewing gum to improve stability.

In another embodiment of the invention, aspartame may be absorbed onto another component, often referred to as a carrier, which is porous and becomes entrapped in the matrix of the porous component. Materials that can be used for absorbing aspartame include, but are not limited to, silicas, silicates, pharmasorb clay, sponge-like beads or microbeads, amorphous carbonates and hydroxides, including aluminum and calcium lakes, vegetable gums and other spray dried materials.

Depending on the type of absorbent material and how it is prepared, the amount of aspartame that can be loaded onto the absorbent will vary. Generally materials such as polymers or sponge-like beads or microbeads, amorphous sugars, and alditols and amorphous carbonates and hydroxides absorb about 10% to about 40% of the weight of the absorbent. Other materials such as silicas and pharmasorb clays may be able to absorb about 20% to about 80% of the weight of the absorbent.

The general procedure for absorbing aspartame onto the absorbent is as follows: an absorbent, such as fumed silica powder, can be mixed in a powder blender and a solution of aspartame can be sprayed onto the powder as the mixing continues. The aqueous solution can be about 5% to 10% aspartame; higher levels may be used if temperatures up to 90° C. are used. Generally water is the solvent, but other solvents such as alcohol could be used if approved for use in food. As the powder mixes, the liquid is sprayed onto the powder. Spraying is stopped before the mix becomes damp. The still flowing powder is removed from the mixer and dried to remove the water or other solvent, then ground to a specific particle size.

After aspartame is absorbed onto an absorbent or fixed onto an absorbent, the fixative/aspartame can be coated by encapsulation. Either full or partial encapsulation may be used, depending on the coating composition used in the process. Full encapsulation may be obtained by coating with a polymer as in spray drying, spray chilling, fluid-bed coating, extrusion, coacervation, or any other standard technique. A partial encapsulation or coating can be obtained by agglomeration using any of the materials discussed above.

Thus, the four methods that can be used to obtain a stabilized aspartame are: (1) encapsulation by spray drying, fluid-bed coating, spray chilling and coacervation to give full or partial encapsulation; (2) agglomeration to give partial encapsulation; (3) fixation or absorption which also gives partial encapsulation; and (4) entrapment by extrusion. These four methods can be combined in any usable manner.

The level of sodium bicarbonate in the gum formula may be about 0.1% to about 10% to provide a dental benefit; levels of effectiveness are obtained even at low levels of 0.1% to about 1%. The amount of aspartame in the gum formula may vary from about 0.01% to about 1%, but preferably adequate sweetness is obtained at 0.1% to about 0.6%; lower levels may be used in a sugar gum formula.

The chewing gum that utilizes the present invention may be any of a variety of different chewing gums.

Chewing gum generally consists of a water insoluble gum base, a water soluble portion, and flavors. The water soluble portion dissipates with a portion of die-flavor over a period of time during chewing. The gum base portion is retained in the mouth throughout the chew.

The insoluble gum base generally comprises elastomers, resins, fats and oils, softeners, and inorganic fillers. The gum base may or may not include wax. The insoluble gum base can constitute approximately 5 to about 95 percent, by weight, of the chewing gum, more commonly, the gum base comprises 10 to about 50 percent of the gum, and in some preferred embodiments, 20 to about 35 percent, by weight, of the chewing gum.

In an embodiment, the chewing gum base of the present invention contains about 20 to about 60 weight percent synthetic elastomer, 0 to about 30 weight percent natural elastomer, about 5 to about 55 weight percent elastomer plasticizer, about 4 to about 35 weight percent filler, about 5 to about 35 weight percent softener, and optional minor amounts (about one percent or less) of miscellaneous ingredients such as colorants, antioxidants, etc.

Synthetic elastomers may include, but are not limited to, polyisobutylene with a GPC weight average molecular weight of about 10,000 to about 95,000, isobutylene-isoprene copolymer (butyl elastomer), styrene-butadiene copolymers having styrene-butadiene ratios of about 1:3 to about 3:1, polyvinyl acetate having a GPC weight average molecular weight of about 2,000 to about 90,000, polyisoprene, polyethylene, vinyl acetate-vinyl laurate copolymer having vinyl laurate content of about 5 to about 50 percent by weight of the copolymer, and combinations thereof.

Preferred ranges are, for polyisobutylene, 50,000 to 80,000 GPC weight average molecular weight, for styrene-butadiene, 1:1 to 1:3 bound styrene-butadiene, for polyvinyl acetate, 10,000 to 65,000 GPC weight average molecular weight with the higher molecular weight polyvinyl acetates typically used in bubble gum base, and for vinyl acetate-vinyl laurate, vinyl laurate content of 10–45 percent.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters of partially hydrogenated rosin, glycerol esters polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids), and combinations thereof.

Colorants and whiteners may include FD&C-type dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5 to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute 5 to about 95% by weight of the chewing gum, more typically, 20 to 80% by weight, and more commonly, 30 to 60% by weight of the gum.

Sugar sweeteners generally include saccharide-containing components commonly known in the chewing gum art, including, but not limited to, sucrose, dextrose, maltose, dextrin, dried invert sugar, fructose, levulose, galactose, corn syrup solids, and the like, alone or in combination.

Sugarless sweeteners include, but are not limited to, sugar alcohols such as sorbitol, mannitol, xylitol, hydrogenated starch hydrolysates, maltitol, and the like, alone or in combination.

In addition to aspartame, other high intensity artificial sweeteners can also be used. Preferred sweeteners include, but are not limited to sucralose, salts of acesulfame, alitame, saccharin and its salts, cyclamic acid and its salts, glycyrrhizin, dihydrochalcones, thaumatin, monellin, and the like, alone or in combination.

Combinations of sugar and/or sugarless sweeteners may be used in chewing gum. Additionally, the softener may also provide additional sweetness such as with aqueous sugar or alditol solutions.

Flavor should generally be present in the chewing gum in an amount within the range of about 0.1–15% by weight of the chewing gum, preferably between about 0.2–5% by weight of the chewing gum, mostly preferably between about 0.5–3% by weight of the chewing gum. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used in the flavor ingredient of the invention. Natural and artificial flavoring agents may be combined in any sensorially acceptable fashion.

Optional ingredients such as colors, emulsifiers, pharmaceutical agents and additional flavoring agents may also be included in chewing gum.

Chewing gum is generally manufactured by sequentially adding the various chewing gum ingredients to any commercially available mixer known in the art. After the ingredients have been thoroughly mixed, the gum mass is discharged from the mixer and shaped into the desired form such as by rolling into sheets, scoring and cutting into pieces. Generally, the ingredients are mixed by first melting the gun base and adding it to the running mixer. The gum base may alternatively be melted in the mixer. Color and emulsifiers can be added at this time.

A softener such as glycerin can be added next along with syrup and part of the bulk portion. Further, parts of the bulk portion may then be added to the mixer. Flavoring agents are typically added with the final part of the bulk portion. The entire mixing process typically takes from five to fifteen minutes, although longer mixing times are sometimes required. Those skilled in the art will recognize that variations of this mixing procedure, or other mixing procedures, may be followed.

By way of example, and not limitation, examples of chewing gums constructed pursuant to the present invention will now be given:

Example 1

An agglomerated aspartame product made with aspartame and hydroxypropylmethyl cellulose (HPMC) was made by first mixing 2500 grams of aspartame and 440 grams of HPMC in a Hobart mixer. Then, 1520 grams of water was slowly added for about 1 hour until the mix was slightly damp. The material was then removed and dried overnight (16 hours) at 170° F. and ground, giving an agglomerated product with 85% active aspartame.

EXAMPLE 2

An extruded aspartame product made with aspartame and medium MW polyvinyl acetate was made by extrusion. Milled aspartame (200 grams) and milled PVAc (800 grams) were dry blended. To this was added 3 grams of Magnesium Stearate to reduce sticking in the feeder. The mix was then extruded to a fiber or ribbon and cooled. After cooling, the product was ground giving an extruded product with 20% active aspartame.

The above two materials were tested in the following gum formulas:

|  | Ex. 3 | Ex. 4 | Ex. 5 | Ex. 6 |
|---|---|---|---|---|
| Base | 25.20 | 25.20 | 25.20 | 25.20 |
| Sorbitol | 51.79 | 51.69 | 50.19 | 51.54 |
| Mannitol | 4.25 | 4.25 | 4.25 | 4.25 |
| Coevaporated Lycasin/Glycerin | 8.50 | 8.50 | 8.50 | 8.50 |
| Glycerin | 8.50 | 8.50 | 8.50 | 8.50 |
| Peppermint Flavor | 1.20 | 1.20 | 1.20 | 1.20 |
| Sodium Bicarbonate | 0.00 | 0.00 | 0.00 | 0.25 |
| Lecithin | 0.16 | 0.16 | 0.16 | 0.16 |
| Free Aspartame | 0.40 | — | — | 0.40 |
| Example 1 | — | 0.50 | — | — |
| Example 2 | — | — | 2.00 | — |

|  | Ex. 7 | Ex. 8 | Ex. 9 | Ex. 10 | Ex. 11 |
|---|---|---|---|---|---|
| Base | 25.20 | 25.20 | 25.20 | 25.20 | 25.20 |
| Sorbitol | 51.44 | 49.94 | 50.79 | 50.69 | 49.19 |
| Mannitol | 4.25 | 4.25 | 4.25 | 4.25 | 4.25 |
| Coevaporated Lycasin/Glycerin | 8.50 | 8.50 | 8.50 | 8.50 | 8.50 |
| Glycerin | 8.50 | 8.50 | 8.50 | 8.50 | 8.50 |
| Peppermint Flavor | 1.20 | 1.20 | 1.20 | 1.20 | 1.20 |
| Sodium Bicarbonate | 0.25 | 0.25 | 1.00 | 1.00 | 1.00 |
| Lecithin | 0.16 | 0.16 | 0.16 | 0.16 | 0.16 |
| Free Aspartame | — | — | 0.40 | — | — |
| Example 1 | 0.50 | — | — | — | — |
| Example 2 | — | 2.00 | — | — | 2.00 |

Figure 3:
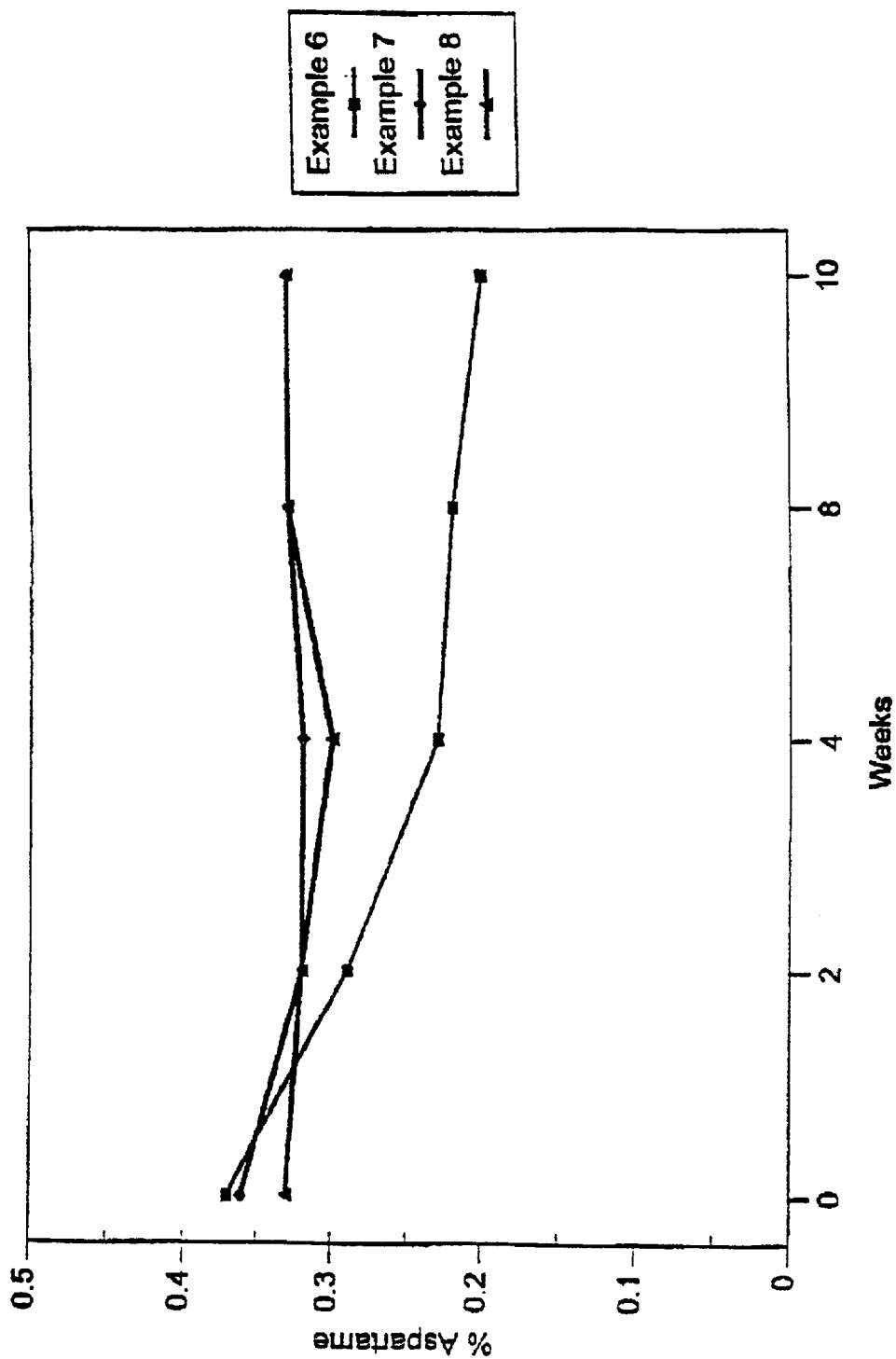
FIG. 3 illustrates graphically aspartame loss with 0.25% sodium bicarbonate, by percent of aspartame over time in weeks.
Figure 4:
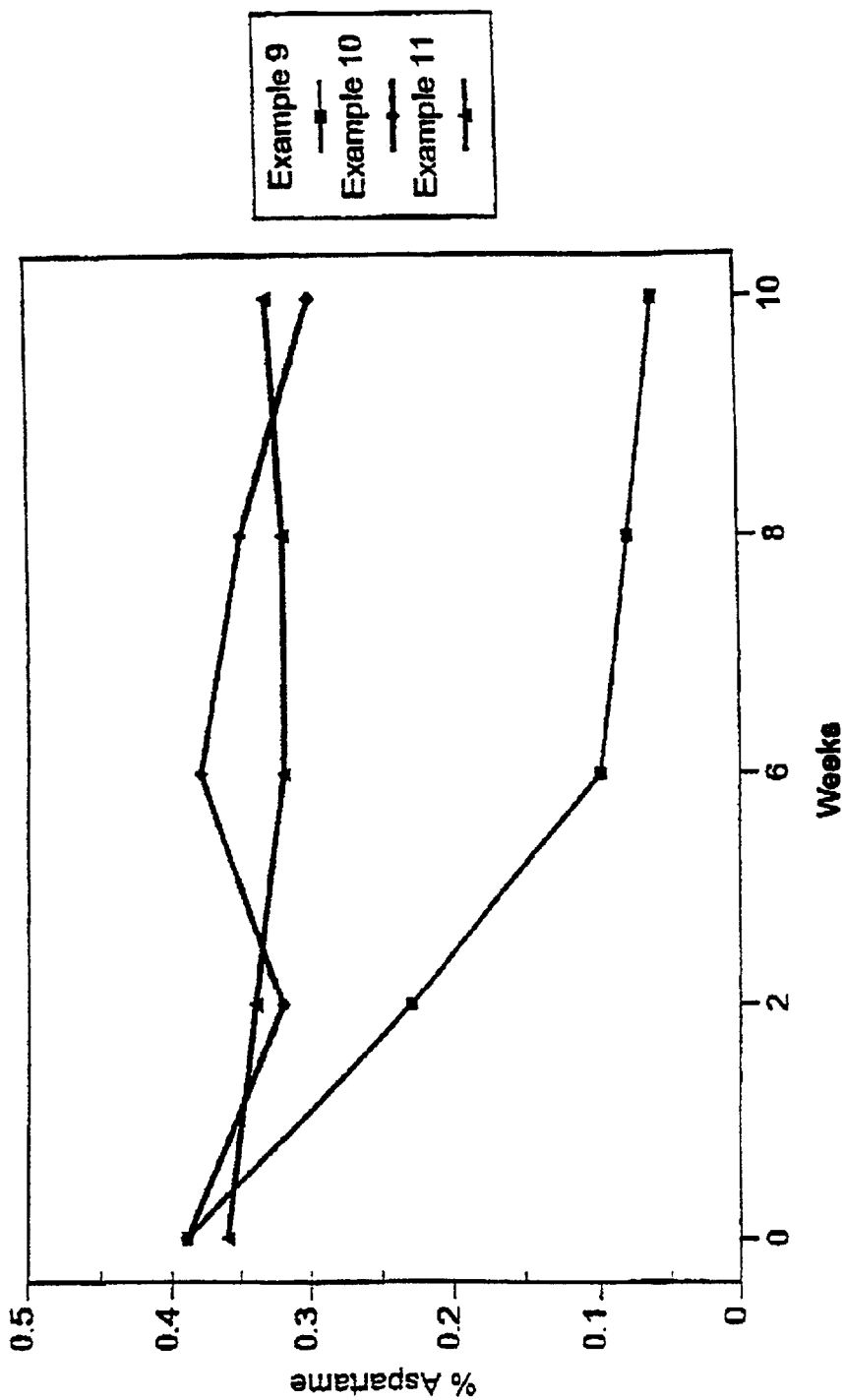
FIG. 4 illustrates graphically aspartame loss with 1% sodium bicarbonate, by percent of aspartame over time in weeks.

Gum samples were sheeted into square pellets and sealed into pouches and stored at 100° F. for 0, 2, 4 or 6, 8, and 10 weeks. After removal, samples were analyzed for % aspartame. Results are illustrated in FIGS. 2, 3, and 4.

Figure 2:
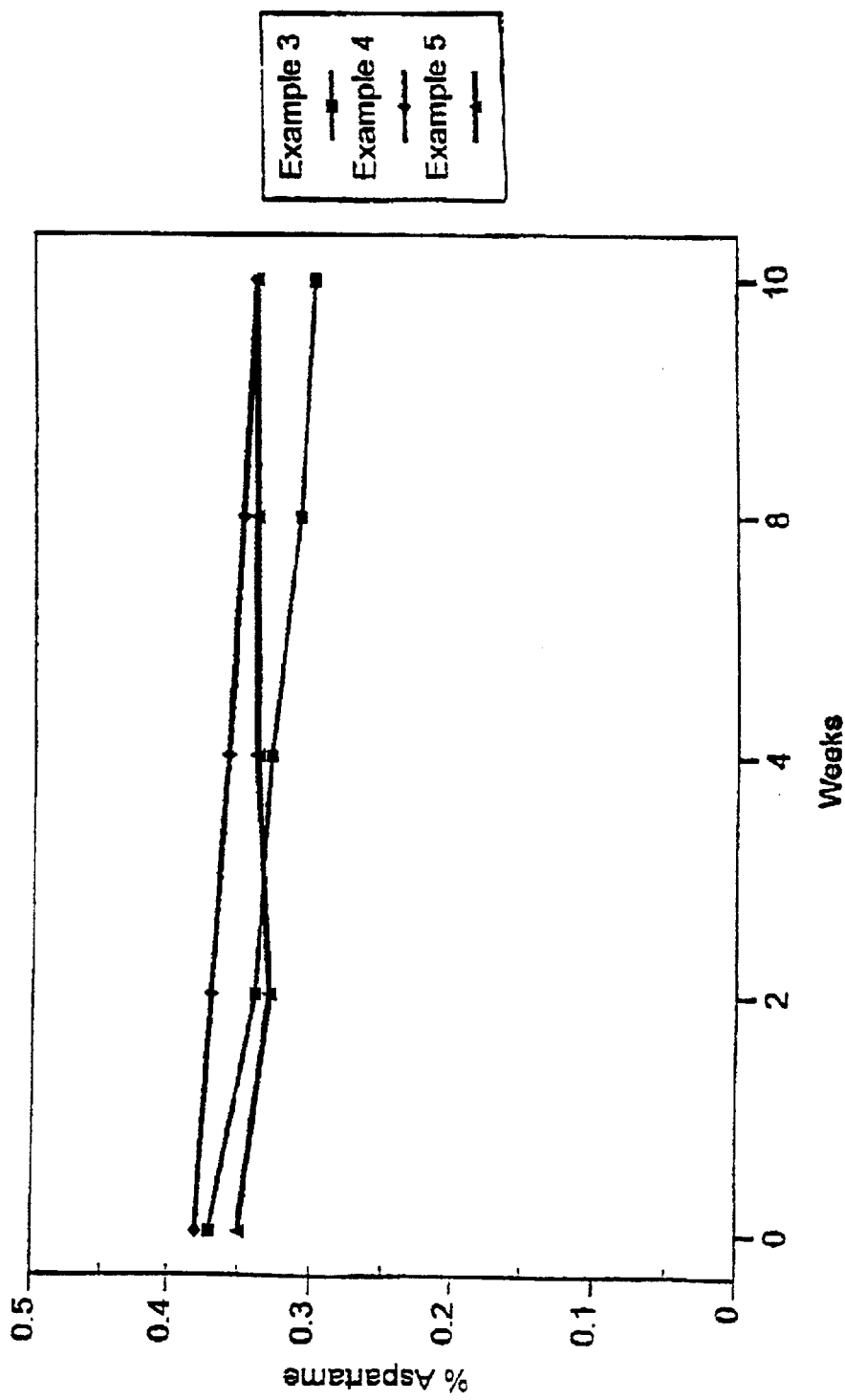
FIG. 2 illustrates graphically aspartame loss with 0% sodium bicarbonate, by percent aspartame over time in weeks.

In FIG. 2 where 0% sodium bicarbonate was used, samples lose a small amount of aspartame, with the encapsulated aspartame being slightly more stable than free aspartame. In FIG. 3, where 0.25% sodium bicarbonate is used, significant loss of free aspartame was noted, but both of the gum samples made with encapsulated aspartame show good stability. Also, in FIG. 4, where 1% sodium bicarbonate is used, there was significant loss of aspartame, but the gum samples made with encapsulated aspartame show good stability.

We claim:

1. A chewing gum comprising:
    a water insoluble gum base portion and a water soluble portion including sodium bicarbonate and a high-intensity sweetener comprising encapsulated aspartame, wherein the sodium bicarbonate and the encapsulated aspartame are admixed within the chewing gum product formed by mixing said water insoluble portion and said water soluble portion.

2. The chewing gum of claim 1 wherein sodium bicarbonate comprises approximately 0.1% to about 1% by weight of the chewing gum.

3. The chewing gum of claim 1 wherein aspartame comprises 0.01% to about 1% by weight of the chewing gum.

4. The chewing gum of claim 1 wherein the aspartame is coated with at least one food grade material selected from the group consisting of shellac, Zein, agar, alginate, cellulose derivatives, dextrin, gelatin, modified starch, acacia and maltodextrin.

5. The chewing gum of claim 1 wherein the encapsulated aspartame comprises at least 20% coating.

6. The chewing gum of claim 1 wherein the moisture level of the chewing gum is not greater than 2%.

7. The chewing gum of claim 1 wherein the aspartame is encapsulated by agglomeration.

8. The chewing gum of claim 1 wherein the aspartame is encapsulated by coating a food grade material onto the aspartame.

9. A chewing gum comprising:
    a water insoluble base portion and a water soluble portion including at least 0.1% by weight sodium bicarbonate and at least 0.01% by weight high-intensity sweetener comprising encapsulated aspartame, wherein the sodium bicarbonate and the encapsulated aspartame are admixed within the chewing gum product formed by mixing the water insoluble portion and the water soluble portion.

10. The chewing gum of claim 9 wherein the aspartame is coated with at least one food grade material selected from the group consisting of shellac, Zein, agar, alginate, cellulose derivatives, dextrin, gelatin, modified starch, acacia and maltodextrin.

11. The chewing gum of claim 9 wherein the encapsulated aspartame comprises at least 20% coating.

12. The chewing gum of claim 9 wherein the moisture level of the chewing gum is not greater than 2%.

13. A method for producing chewing gum including aspartame comprising the steps of:
    adding to a water insoluble base portion, a water soluble portion including sodium bicarbonate and a high intensity sweetener comprising encapsulated aspartame, wherein the sodium bicarbonate and the encapsulated aspartame are admixed within the chewing gum product formed by mixing the water insoluble portion and the water soluble portion.

14. The method of claim 13 wherein the encapsulated aspartame and sodium bicarbonate is added to the water insoluble base portion with a flavor.

15. The method of claim 13 including the step of encapsulating the aspartame by coating a food grade material onto the aspartame.

16. The method of claim 13 including the step of encapsulating the aspartame by agglomerating an agent onto the aspartame.

17. The method of claim 13 including the step of encapsulating the aspartame using a two-step process.

18. The method of claim 13 including the step of encapsulating the aspartame using a process wherein aspartame is absorbed onto another component.

19. The chewing gum of claim 13 wherein the moisture level of the chewing gum is not greater than 2%.

* * * * *